United States Patent
Vachss et al.

(10) Patent No.: US 7,570,349 B2
(45) Date of Patent: Aug. 4, 2009

(54) CARS/ABSORPTION DUAL MODE ELECTRO-OPTIC SENSOR

(75) Inventors: Frederick R. Vachss, Thousand Oaks, CA (US); Robert A. Smith, Hampton Cove, AL (US)

(73) Assignee: The Boeing Company, Chicago, IL (US)

( * ) Notice: Subject to any disclaimer, the term of this patent is extended or adjusted under 35 U.S.C. 154(b) by 303 days.

(21) Appl. No.: 11/748,748

(22) Filed: May 15, 2007

(65) Prior Publication Data

US 2008/0285008 A1    Nov. 20, 2008

(51) Int. Cl.
*G01N 21/00* (2006.01)
(52) U.S. Cl. .......................... 356/73; 356/301
(58) Field of Classification Search .................... 356/73, 356/301
See application file for complete search history.

(56) References Cited

U.S. PATENT DOCUMENTS 4,512,660 A    4/1985   Goldberg
4,555,176 A    11/1985  Moore et al.
7,352,458 B2 *  4/2008   Xie et al. ..................... 356/301
2006/0078011 A1 4/2006  Lucht et al.
2007/0088219 A1 4/2007  Xie et al.

OTHER PUBLICATIONS

D.A. Akimov et al., Photonic-crystal fiber sources for nonlinear spectroscopy, Vibrational Spectroscopy, Jun. 11, 2006, pp. 33-40, vol. 42.

* cited by examiner

*Primary Examiner*—Gregory J Toatley, Jr.
*Assistant Examiner*—Abdullahi Nur
(74) *Attorney, Agent, or Firm*—Haynes and Boone, LLP.

(57) ABSTRACT

A target gas sensing system includes a single source at a first location for generating two light beams having first and second frequencies wherein the difference between the first and second frequencies is the Raman frequency of the target gas. A difference frequency generator outputs the two light beams having the first frequency, the second frequency, and a third light beam having a third frequency that is the difference between the first and second frequencies. The first, second, and third light beams are directed toward the target gas. An input optic directs light from the third light beam, after interacting with the target gas, to a receiver for absorption spectroscopy processing, directs a fourth light beam from the target gas to a receiver for coherent anti-Stokes Raman processing, wherein the fourth light beam has a frequency of twice the first frequency minus the second frequency.

25 Claims, 2 Drawing Sheets

CARS/ABSORPTION DUAL MODE ELECTRO-OPTIC SENSOR

TECHNICAL FIELD

The present disclosure relates generally to optical techniques for sensing gaseous substances.

BACKGROUND

Sensing of extremely low concentrations of gases is required for effective detection of various chemical or explosive hazards. The hazardous nature of the compounds of interest makes detection at a safe standoff distance highly desirable. Individual spectroscopic laser techniques for gas sensing, while effective, typically do not provide the sensitivity required for practical standoff hazardous gas detection.

Various spectroscopic techniques may be used in standoff laser detection of hazardous substances. Sensors capable of several techniques simultaneously or cooperatively often yield superior performance results. Among the most useful of these techniques are absorption spectroscopy and Coherent Anti-Stokes Raman Scattering (CARS).

Coherent anti-Stokes Raman spectroscopy (CARS) is a form of spectroscopy used primarily in chemistry, physics and related fields. It is closely related to Raman spectroscopy and lasing processes, but involves a light amplification process that dramatically improves the signal. Two laser beams, one at an excitation (pump) frequency and the second at a frequency that produces Stokes Raman scattering, interact coherently in a sample (e.g., a gas), producing a strong scattered beam at the anti-Stokes frequency. The CARS process taking place in the sample is a third-order nonlinear optical process. The anti-Stokes frequency is resonantly enhanced when the difference in incident laser photon energies coincides with the frequency of a Raman resonance, which provides the intrinsic vibrational contrast mechanism. The anti-Stokes spectra contain information that relates to gas species concentration. The non-linear wave mixing is a vector process, and the laser like anti-Stokes signal leaves the diagnostic volume in a prescribed direction that depends on the vector angles of the pump and Stokes beams. Since the signal is laser like, it can be focused.

Absorption spectroscopy is based on the absorption of photons by one or more substances present in a sample, which can be a solid, liquid, or gas, and subsequent excitation of electron(s) from one energy level to another in that substance. The wavelength at which the incident photon is absorbed is determined by the difference in the available energy levels of the different substances present in the sample; it is the selectivity of absorbance spectroscopy—the ability to generate photon (light) sources that are absorbed by only some of the components in a sample at a specific wavelength—that gives absorbance spectroscopy much of its utility. In one implementation, known as differential absorption, a source laser that is tunable may generate a wavelength that is strongly absorbed by the target, e.g., a gas. Tuning the laser to another wavelength may generate a laser line that is not absorbed. By alternately modulating between the two wavelengths and comparing the ratio of the absorbed to unabsorbed wavelengths, a measure of the concentration of the absorbing gas may be directly obtained.

Differential Absorption Laser Imaging Detection and Ranging (i.e., DIfferential Absorption LIDAR, or DIAL) is a variation of the above technique used in pollution and gas sensing. Two wavelengths of light are used in the same manner as just described, but light is transmitted in pulses and the pulse time-of flight is additionally used to determine distance to the target sample. The light beam is modulated between two wavelengths, one at the absorption wavelength, and a second of a nearby wavelength that is not absorbed. For example, in a gas target, a measurement of the ratio of the pulsed light scattered or transmitted at both wavelengths yields information about the range (distance to the target gas) and concentration of the gas as a function of distance. The range to the gas is determined by measuring the time delay between transmission of a pulse and detection of the scattered signal.

CARS and Differential Absorption spectroscopy are two such spectroscopic techniques which may be used effectively in combination for gas sensing, but these techniques typically require their own individual laser sources and sensors. Typically these two methods require separate laser sources and detectors, with an associated increase in system complexity, volume, and cost.

Practical detection systems using this combination would benefit greatly from the reduction in system size, complexity and cost that would result if the two techniques could be employed using the same laser source.

SUMMARY

Methods and systems for sensing a target gas with a single laser source device may be used for two distinct spectroscopic standoff detection techniques. This device uses intrinsic properties of a nonlinear optical Difference Frequency Generator (DFG). Specifically, when a DFG is used to mix radiation at frequencies $f_1$ and $f_2$ to produce a laser output at a frequency of $f_{out}$, it also transmits or amplifies, as a byproduct, the laser radiation at the two input frequencies, where $f_{out}=f_1-f_2$. The direct laser output at frequency $f_{out}$ may be used to sense gases with absorptions at this frequency. By tuning $f_{out}$ across a range which includes frequencies at which substantially no absorption occurs, a differential (i.e., ratiometric) measurement that is independent of laser power fluctuations may be obtained.

In addition, however, if the amplified intermediate output frequencies $f_1$ and $f_2$ are used to probe the gas and if the gas has a Raman spectral transition at $f_{out}$, then these two frequencies will interact with the gas in a Coherent Anti-Stokes Raman (CARS) process and produce scattered laser light with frequency $f_3=f_1+f_{out}=2f_1-f_2$. As the CARS spectrum and the direct absorption spectrum of any molecule are distinct, this provides a means of obtaining two separate laser spectroscopic analyses of a gas using a single DFG laser source. In particular, when frequency $f_{out}$ from this laser source is tuned across a region with many potential absorption and Raman transitions, both CARS and differential absorption spectra of a target gas may be collected simultaneously via this method.

A single Difference Frequency Generator (DFG) laser source may be configured so that the beams at all frequencies exiting the device are directed at a target gas. After the various beams pass through the gas, they are either directed into detectors sensitive to the various frequencies in a transmission configuration, or light scattered from these beams by the gas is directed into detectors in the case of a reflective/scattering configuration. Dichroic filters and beam splitters are used as necessary to separately direct the beams at frequency $f_{out}$ and $f_3$ into individual detectors that sense the absorption and CARS spectrum of the gas separately.

Systems and methods are disclosed herein to provide remote (i.e., standoff) gas sensing using two spectroscopic techniques, i.e., standard differential absorption spectroscopy and the other Coherent Anti-Stokes Raman Spectroscopy (CARS), based on one laser system.

More specifically, in accordance with one embodiment, a method of sensing includes providing a first light beam having a frequency $f_1$ and a second light beam having a frequency $f_2$ to a difference frequency generator (DFG). The DFG generates a light beam of a difference frequency $f_{out}=f_1-f_2$, an amplified beam of frequency $f_2$, and a transmitted beam of frequency $f_1$, all of which are coupled to an output optic. The combined beams are directed to a gas target sample. Light transmitted through or scattered from the target sample is received by an input optic, where the received light has the frequencies $f_1$, $f_2$, $f_{out}$, and a frequency $f_3=2f_1-f_2$, wherein frequency $f_3$ is generated by interaction of the target gas with the beams of frequencies $f_1$ and $f_2$. A dichroic filter may transmit only light of frequencies $f_{out}$ and $f_3$. Light with frequency $f_3$ is directed into a Coherent Anti-Stokes Raman Scattering (CARS) detector by passing it through a dichroic beam splitter, which separates light of frequency $f_3$ from light of frequency $f_{out}$. Light of frequency $f_{out}$ is directed to a Differential Absorption detector.

In accordance with an embodiment, a sensing system includes a first laser source having a light beam with an output frequency $f_1$, a second laser source having a light beam with an output frequency $f_2$, and a difference frequency generator (DFG) for receiving the light beams of frequency $f_1$, and $f_2$ and outputting a combined beam of light with frequency $f_{out}=f_1-f_2$, a light beam of frequency $f_1$, and an amplified light beam of frequency $f_2$. An output optic directs the combined beams at a target gas, and an input optic receives light scattered from or transmitted through the target gas. The received light comprises light having the frequencies $f_1$, $f_2$, $f_{out}$, and a frequency $f_3=2f_1-f_2$, wherein frequency $f_3$ is generated by interaction of the target gas with the beams of frequencies $f_1$ and $f_2$. A dichroic filter removes light of frequencies $f_1$ and $f_2$ and transmits light of frequencies $f_{out}$ and $f_3$. A dichroic beam splitter separates light of frequency $f_{out}$ from light of frequency $f_3$, directs the light of frequency $f_{out}$ to a differential absorption detector, and directs light of frequency $f_3$ to a CARS detector.

The scope of the disclosure is defined by the claims, which are incorporated into this section by reference. A more complete understanding of embodiments will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

Embodiments and their advantages are best understood by referring to the detailed description that follows. It should be appreciated that like reference numerals are used to identify like elements illustrated in one or more of the figures.

DETAILED DESCRIPTION

Figure 1:
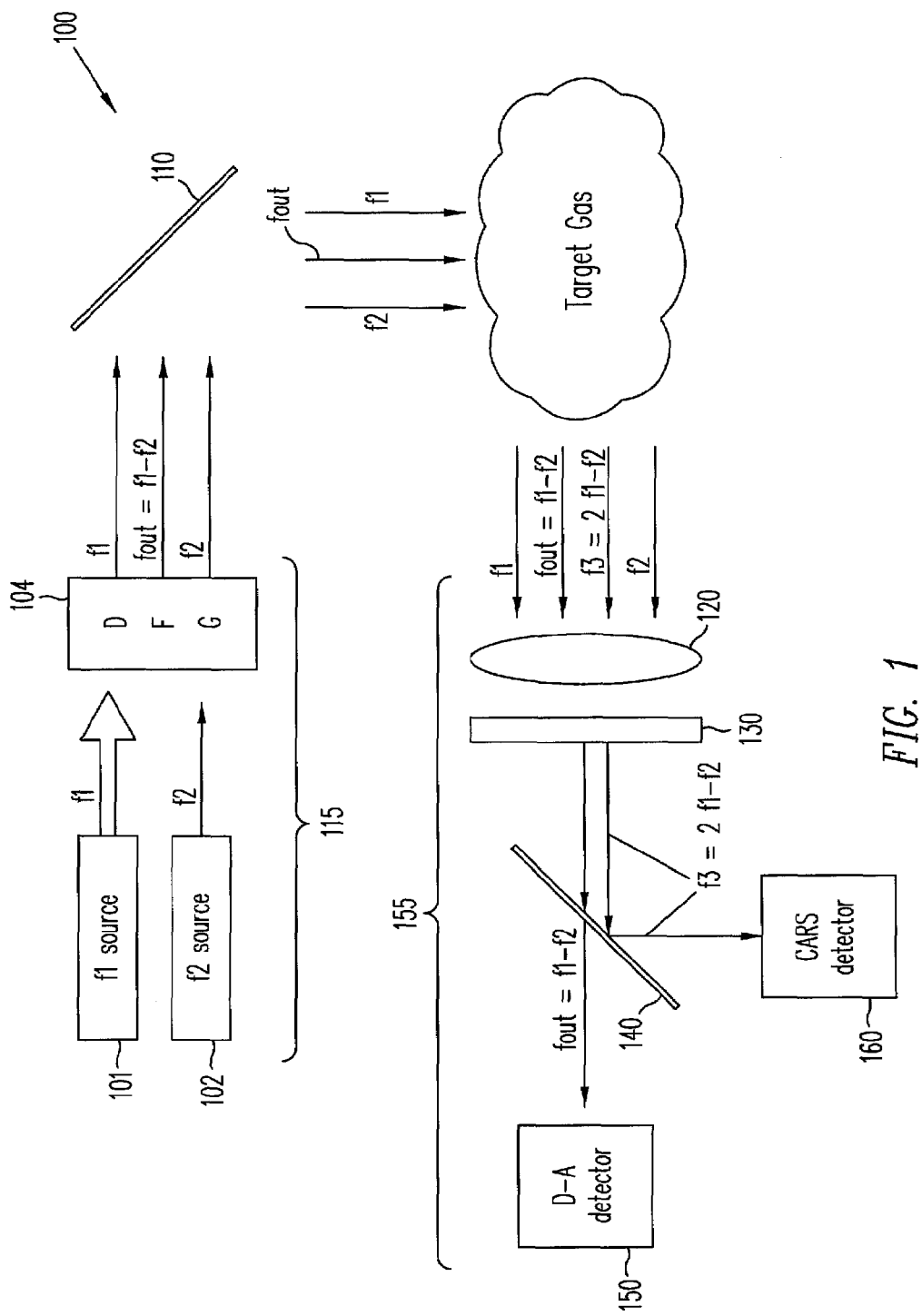
FIG. 1 illustrates a CARS/Absorption Spectroscopy dual mode sensor in accordance with an embodiment of the present disclosure.

Referring to FIG. 1, in accordance with an embodiment of the present disclosure, a CARS/Absorption Spectroscopy dual mode sensor system 100 includes a beam generator 115 and a detector system 155. Beam generator 115 includes a first laser source 101 having a light beam with an output frequency $f_1$ and a second laser source 102 having a light beam with an output frequency $f_2$. Conventionally, one source may be designated as a pump laser, e.g., laser source 101, as will be made clear below. In beam generator 115, light beams from laser source 101 and 102 enter an optical difference frequency generator (DFG) 104 which is a non-linear optical device for mixing light beams as follows: DFG 104 generates a combined output beam of light that includes a light beam with frequency $f_{out}=f_1-f_2$ as a result of non-linear mixing, an amplified light beam of frequency $f_2$, which is also the result of the non-linear properties of DFG 104, and a light beam of frequency $f_1$, which may be somewhat attenuated as a result of mixing with $f_2$ to form $f_{out}$ and to pump $f_2$ to a greater amplitude. Beam generator 115 further includes an output optic 110 which directs the combined beams at a target gas.

FIG. 1 indicates all light beams of frequency $f_1$, $f_2$, $f_{out}$ by individual arrows. In fact, the light beams from laser sources 101 and 102 may be transmitted as separate beams combined as a single collinear beam before being received by DFG 104, or the beam combining may be incorporated as part of the DFG (not shown) and light beams of frequency $f_1$, $f_2$ and $f_{out}$ which are output from DFG 104 may be collinear as well. In this case, where nonlinear mixing is taking place to provide $f_{out}$, it is advantageous for the combined input beam to DFG 104 to have a high power density to increase the mixing efficiency. In particular, the pump laser beam is so designated because it has a high beam intensity to begin with. It may be sufficient if the combined beam is collimated and small, or else the combined beam may be focused at a location inside the nonlinear optical medium of DFG 104, thereby increasing the power density and conversion efficiency.

Output optic 110 may be implemented in various ways, and is shown only schematically in FIG. 1. For example, if the combined beam output from DFG 104 is collimated, output optic may simple comprise a series of relay mirrors (not shown) to direct the beam at the target gas. If, however, the combined beam is divergent when output from DFG 104, output optic may further include a system of lenses (i.e., as transmissive lenses or focusing mirrors, not shown) to control the expansion and collimation of the combined beam to a desired diameter. Furthermore, as will be discussed in more detail below, if it is desired to focus all or portions of the light output from DFG 104 at the target gas where, again, because a nonlinear optical mixing interaction is taking place, the system of lenses may be configured to focus only portions of the light beam at a distance. A projection telescope (not shown) may conveniently be included in output optic 110 for this purpose. In particular, since the excitation of light of frequency $f_3=2f_1-f_2$ is a non-linear process, it may be advantageous to focus light of frequencies f1 and $f_2$ at the target gas. At a focal point located inside the target gas, the light wave interaction will be most efficient due to the higher intensity of focused light.

Absorption detection, on the other hand, benefits from the beam of frequency $f_{out}$ being configured at the target gas to irradiate as much of the absorbing volume of gas as may be practicable, so that a collimated or divergent beam may be preferred for light of frequency $f_{out}$. Therefore, output optic 110 may comprise a system of dichroic beam splitter and beam control optical components to prepare light at frequencies $f_1$ and $f_2$ differently from light at frequency $f_{out}$.

Detector system 155 includes an input optic 120 which receives light scattered from or transmitted through the target gas. Input optic 120 may include, for example, relay mirrors and a telescope (both not shown), where the aperture of the primary mirror provides signal gain in proportion to its collection area. Therefore, the size of the telescope may be selected as a design trade-off between, cost, size (e.g., portability) and gain-sensitivity requirements. Additionally, the telescope may further include additional optics to collimate or focus the collected light on the sensors (discussed below).

The received light comprises light having frequencies $f_1$, $f_2$, $f_{out}$, and a frequency $f_3=2f_1-f_2$, wherein frequency $f_3$ is generated by interaction of the target gas with the beams of frequencies $f_1$ and $f_2$. Detector system 155 further includes a dichroic filter 130 which may remove light of frequencies $f_1$ and $f_2$, but principally transmits light of at least frequencies $f_{out}$ and $f_3$. Detector system 155 further includes a dichroic beam splitter 140 which separates light of frequency $f_{out}$ from light of frequency $f_3$, directs the light of frequency $f_{out}$ to a differential absorption detector 150, and directs light of frequency $f_3$ to a CARS detector 160, both of which are included in detector System 155. Dichroic filters and beam splitters are well known in the art.

It is a particular benefit of system 100 that, as a result of the beam generation system being a tunable source of monochromatic laser light, considerable simplification occurs in detector system 155. It is known, by prior selection of frequency $f_{out}$, that absorption detector 150 requires a sensing element and optical components tailored to a particular range of wavelengths. The same is true for CARS detector 160, which may be in the same or a different wavelength range.

As an example of selection of frequencies $f_1$, $f_2$, $f_{out}$, and $f_3$, consider an application for detection of vapors from explosive compounds. It is known that such compounds may have infrared absorption bands in the 7-9 micrometer wavelength range. Telecommunications diode laser sources are readily available at wavelengths of $\lambda 1=1.55$ micrometers and $\lambda 2 \sim 1.95$ micrometers (where both are tunable). DFG 104 will then produce a beam of frequency $f_{out}=f_1-f_2$ corresponding to a wavelength of ~7.56 micrometers. This may be readily detected in absorption detector 150 with a long wavelength infrared sensor, such as HgCd, or HgCdTe. The CARS generation of light at $f_3=2f_1-f_2$ will have a wavelength of ~1.29 micrometers, which may be readily detected in CARS detector 160 with a short wavelength infrared sensor, such as InGaAs.

Sensing system 100 may be arranged with both beam generator 115 and detector system 155 located at substantially the same position, so that Detector System 155 receives substantially backscattered light at the various frequencies. Alternatively, detector system 155 may be at a different location than beam generator 115, so that light received may be any combination of light scattered and transmitted when interacting with the target gas.

In beam generator 115, laser source 102 may be a tunable laser adapted to provide light of at least a frequency $f_{2a}$ and a frequency $f_{2b}$. Therefore, it will be appreciated that frequency $f_{out}$ may be, alternatively, $f_{outa}=f_1-f_{2a}$ or $f_{outb}=f_1-f_{2b}$. In either case, differential absorption detector 150 is adapted to detect $f_{outa}$ and $f_{outb}$.

Laser source 102 may be temporally modulated to form pulses of light, and detector system 155 may be coupled to beam generator 115 to measure time-of-flight between the two, thus establishing the range (i.e., distance) to the target gas. Since the target gas may occupy an extended volume, the time-of-flight signal may provide information concerning the concentration of the target gas as a function of distance or position. The geometric configuration of beam generator 115 and detector system 155 are known, so that ranging may be accurately determined. Many applications may require detection at a range of several hundred meters, such as in detection of toxic gas from a safe distance. As an example of time-of-flight ranging, assume the distance is 500 meters to the target gas, and both beam generator 115 and detector system 155 are co-located. Therefore, the total time of flight corresponding to 1000 meters round-trip is T=1000 m/3×10^8 m/s=3.33 microseconds. A pulse of time length 10 nanoseconds would have a physical pulse length of about 3 meters, which establishes an approximate value of the accuracy of ranging the distance to the gas.

If laser source 102 provides light of a single frequency $f_2$, then $f_2$ may be selectively chosen so that absorption by the target gas is enhanced at frequency $f_{out}$. Differential detector 150 then makes a measurement of absorption that is not normalized against a reference signal.

Alternatively, if the temporal modulation of laser source 102 also includes switching between at least two frequencies $f_{2a}$, and $f_{2b}$, where one frequency, say $f_{outa}$ is absorbed by the target gas, while frequency $f_{outb}$ is insubstantially absorbed, a normalized measure of gas concentration may be determined by taking the ratio of measured signal intensities at each of the frequencies, i.e., $I_{fouta}/I_{foutb}$. If the pulse lengths and generated amplitudes at each frequency are the same or in known relation, and the beam shape of both (e.g., diameter and dispersion) are the same or in known relationship, then an absolute measure of gas concentration may be determined by the ratio measurement.

Laser source 101 and laser source 102 may both be modulated temporally to provide light pulses that are generated in phase at frequencies $f_1$ and $f_2$ (e.g., $f_{2a}$ and $f_{2b}$) This may be particularly beneficial since pulsed laser sources may generally have higher peak amplitude, which further enhances the non-linear pumping efficiency in difference frequency generator 104 to both amplify light of frequency $f_{2a,b}$ and generate, via wave mixing, pulsed beams of light at frequencies $f_{outa,b}$.

Laser sources 101 and 102 may, alternatively, be a single laser adapted to operate in multi-wavelength operation, where the output wavelengths correspond to frequencies $f_1$, $f_{2a}$ and $f_{2b}$. Alternatively, laser sources 101 and 102 may be a single wavelength laser source (not shown) coupled to a non-linear optical element (not shown) adapted to generate light beams at frequencies $f_1$, $f_{2a}$ and $f_{2b}$.

Differential absorption detector 150 measures a decrease in signal with increased concentration of the target gas due to increased absorption. CARS detector 160 measures an increase in signal with increased gas concentration due to non-linear optical wave mixing that takes place in the presence of the gas. Furthermore, as a result of quantum mechanical selection rules that may be different for absorption processes at frequency $f_{out}$ and CARS scattering frequency $f_3$, signals may be detected simultaneously at both differential absorption detector 150 and CARS detector 160, or only one or the other. Therefore, it will be appreciated that the two methods of sensing, which are derived from the same laser sources, provides a more sensitive and comprehensive measure of gas concentration than with a single type of detector, and simultaneously takes advantage of a single laser system to operate both detectors and sensing modes.

It should be appreciated in the foregoing that operation of laser sources 101 and 102 may be interchangeable, whereby laser source 101 may be tunable to provide the same result for $f_{out}$ and $f_3$, and furthermore, laser source 102 may be regarded as the pump laser. For convenience, laser source 101 is regarded as the pump laser at a fixed frequency $f_1$ and laser source 102 is regarded as a frequency tunable laser at $f_2$.

Figure 2:
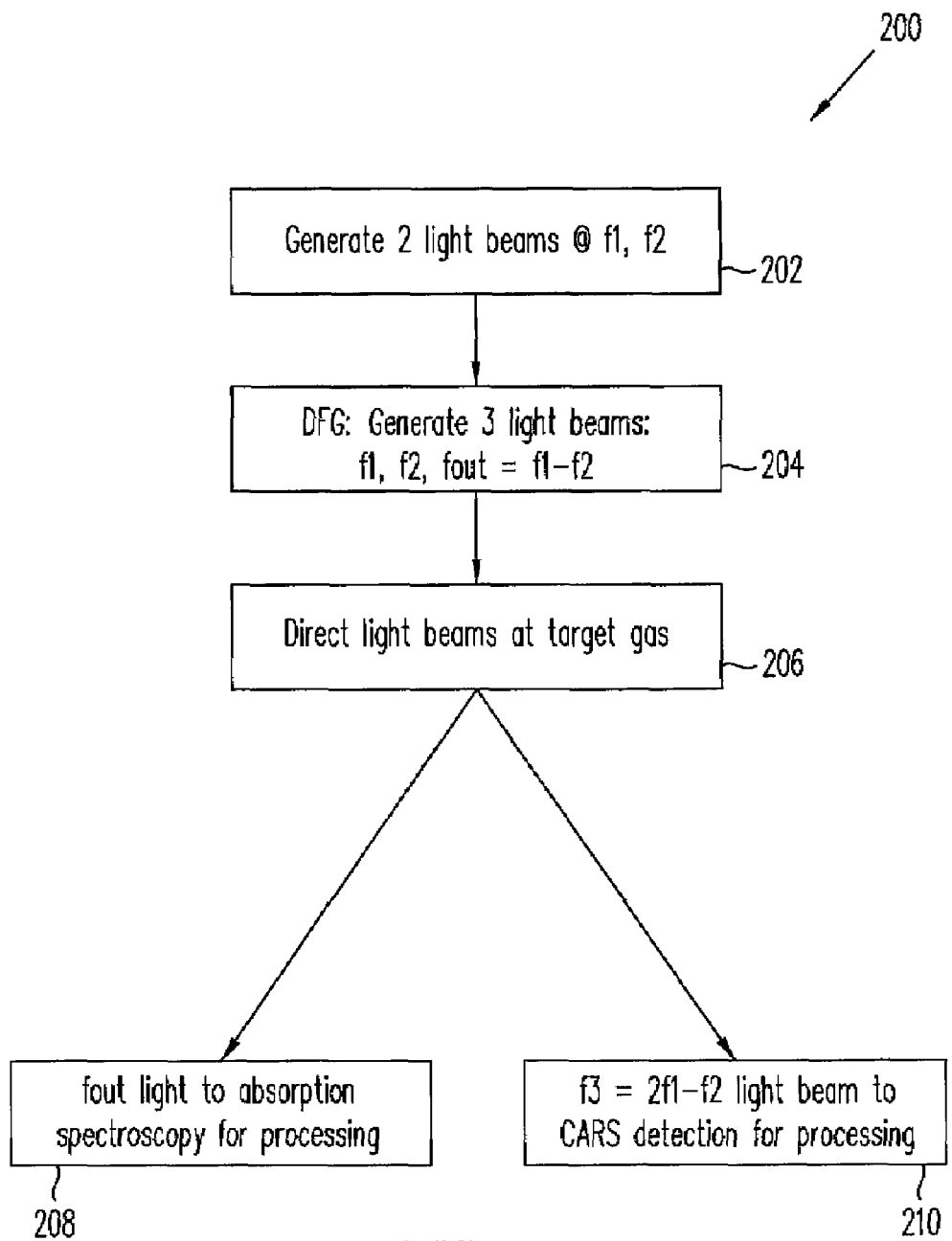
FIG. 2 is a flow chart of a method of sensing a target gas in accordance with an embodiment of the present disclosure.

FIG. 2 is a flowchart 200 showing one embodiment of the present invention. First, a light beam at a first frequency $f_1$ and a light beam at a second frequency $f_2$ is generated (block 202), where the frequency difference is the Raman frequency of a target gas. Next, three light beams are generated (block 204), with the first frequency $f_1$, the second frequency $f_2$, and a frequency that is the difference of the first and second frequencies. The three beams are then directed to a target gas (block 206), such as with optics. The light beam having the difference frequency, after passing through or scattering from the target gas, is directed, such as with optics, to an absorption spectroscopy detector for processing (block 208). A fourth light beam that is generated by the interaction with the target gas of the first and second light beams, having a frequency $f_3$ that is twice the first frequency $f_1$ minus the second frequency $f_2$, is directed, such as with optics, to a CARS detector for processing (block 210).

Embodiments described above illustrate but do not limit the invention. It should also be understood that numerous modifications and variations are possible in accordance with the principles of the present invention. Accordingly, the scope of the invention is defined only by the following claims

We claim:

1. A method of sensing a target gas, comprising:
    generating two light beams at a first frequency and a second frequency from a single source at a first location, wherein the difference between the first and second frequencies is the Raman frequency of the target gas;
    generating, from the two light beams, a first light beam having the first frequency, a second light beam having the second frequency, and a third light beam having a third frequency that is the difference between the first and second frequencies;
    directing the first, second, and third light beams toward the target gas;
    directing light from the third light beam, after interacting with the target gas, to a receiver for absorption spectroscopy processing; and
    directing a fourth light beam from the target gas to a receiver for coherent anti-Stokes Raman processing, wherein the fourth light beam has a frequency of twice the first frequency minus the second frequency.

2. The method of claim 1, wherein the receiver for absorption spectroscopy processing and the receiver for coherent anti-Stokes Raman processing are at a location substantially co-located with the first location of the single source, and the directing of third and fourth light beams are in a substantially backscattered direction from the target gas.

3. The method of claim 1, wherein the receiver for absorption spectroscopy processing and the receiver for coherent anti-Stokes Raman processing are at a second location different from the first location of the single source, and the directing of third and fourth light beams are in a substantially transmissive and/or sideways or forward scattered direction from the target gas.

4. The method of claim 1, wherein the receiver for absorption spectroscopy processing measures the intensity of the light beam having the third frequency after interaction with the target gas.

5. The method of claim 4, wherein the light beam having the second frequency further alternates temporally between an alpha second frequency and a beta second frequency, thereby alternating the third frequency of the third light beam to an alpha third frequency and a beta third frequency.

6. The method of claim 5, wherein the absorption spectroscopy measures the relative intensities of the light beams having the alpha third frequency and the beta third frequency, and wherein a differential absorption corresponds to the ratio of the intensities.

7. The method of claim 5, wherein the alternating light beams having the alpha second frequency and beta second frequency are pulsed, and the absorption spectroscopy processing includes measuring the time-of-flight of the light beam pulses having the alpha third frequency and the beta third frequency between the single source and the receiver for absorption spectroscopy.

8. The method of claim 1, wherein the receiver for coherent anti-Stokes Raman processing measures the intensity of the light beam having the fourth frequency.

9. The method of claim 1, wherein the first and second light beams are provided by a first and second laser.

10. The method of claim 1, wherein the single source of the first and second light beams is a single laser providing light beams having multiple frequencies.

11. The method of claim 1, wherein the single source of the first and second light beams is a single laser having a single frequency coupled to a non-linear optical element adapted to provide the first light beam having the first frequency and the second light beam having the second frequency.

12. A target gas sensing system comprising:
    a single source at a first location for generating two light beams having a first frequency and a second frequency wherein the difference between the first and second frequencies is the Raman frequency of the target gas;
    a difference frequency generator for generating from the two light beams a first light beam having the first frequency, a second light beam having the second frequency, and a third light beam having a third frequency that is the difference between the first and second frequencies;
    a light beam director for directing the first, second, and third light beams toward the target gas; and
    an input optic for directing light from the third light beam, after interacting with the target gas, to a receiver for absorption spectroscopy processing and directing the fourth light beam from the target gas to a receiver for coherent anti-Stokes Raman processing, wherein the fourth light beam has a frequency of twice the first frequency minus the second frequency.

13. The system of claim 12, wherein the receiver for absorption spectroscopy processing and the receiver for coherent anti-Stokes Raman processing are at a location substantially co-located with the first location of the single source, and the directing of third and fourth light beams are in a substantially backscattered direction from the target gas.

14. The system of claim 12, wherein the receiver for absorption spectroscopy processing and the receiver for coherent anti-Stokes Raman processing are at a second location different from the first location of the single source, and the directing of third and fourth light beams are in a substantially transmissive and/or sideways or forward scattered direction from the target gas.

15. The system of claim 12, wherein the receiver for absorption spectroscopy processing measures the intensity of the light beam having the third frequency after interaction with the target gas.

16. The system of claim 15, wherein the light beam having the second frequency further alternates temporally between an alpha second frequency and a beta second frequency, thereby alternating the third frequency of the third light beam to an alpha third frequency and a beta third frequency.

17. The system of claim 16, wherein the absorption spectroscopy measures the relative intensities of the light beams having the alpha third frequency and the beta third frequency, and wherein a differential absorption corresponds to the ratio of the intensities.

18. The system of claim 16, wherein the alternating light beams having the alpha second frequency and beta second frequency are pulsed, and the absorption spectroscopy processing includes measuring the time-of-flight of the light beam pulses having the alpha third frequency and the beta third frequency between the single source and the receiver for absorption spectroscopy.

19. The system of claim 12, wherein the receiver for coherent anti-Stokes Raman processing measures the intensity of the light beam having the fourth frequency.

20. The system of claim 12, wherein the first and second light beams are provided by a first and second laser.

21. The system of claim 12, wherein the single source of the first and second light beams is a single laser providing light beams having multiple frequencies.

22. The system of claim 12, wherein the single source of the first and second light beams is a single laser having a single frequency coupled to a non-linear optical element adapted to provide the first light beam having the first frequency and the second light beam having the second frequency.

23. A target gas sensing system comprising:
   means capable of generating two light beams having a first frequency and a second frequency wherein the difference between the first and second frequencies is the Raman frequency of the target gas;
   means capable of generating from the two light beams a first light beam having the first frequency, a second light beam having the second frequency, and a third light beam having a third frequency that is the difference between the first and second frequencies;
   means capable of absorption spectroscopy processing light from the third light beam, after interacting with the target gas; and
   means capable of coherent anti-Stokes Raman processing a fourth light beam from the target gas, wherein the fourth light beam has a frequency of twice the first frequency minus the second frequency.

24. The system of claim 23, further comprising means capable of directing the first, second, and third light beams toward the target gas.

25. The system of claim 23, further comprising means capable of directing light from the third light beam, after interacting with the target gas, to the means for absorption spectroscopy processing and for directing the fourth light beam to the means for coherent anti-Stokes Raman processing.

* * * * *